US005088476A

United States Patent [19]

Burton

[11] Patent Number: 5,088,476

[45] Date of Patent: * Feb. 18, 1992

[54] GRAVITY TRACTION DEVICE WITH A SAFETY STRAP AND BASE SUPPORT AND METHOD

[75] Inventor: Charles V. Burton, Excelsior, Minn.

[73] Assignee: Spinal Designs International, Inc., Minneapolis, Minn.

[ * ] Notice: The portion of the term of this patent subsequent to Jul. 23, 2008 has been disclaimed.

[21] Appl. No.: 733,669

[22] Filed: Jul. 22, 1991

Related U.S. Application Data

[63] Continuation-in-part of Ser. No. 609,065, Oct. 29, 1990, Pat. No. 5,033,459, which is a continuation of Ser. No. 488,534, Feb. 28, 1990, abandoned, which is a continuation of Ser. No. 301,172, Jan. 24, 1989, abandoned.

[51] Int. Cl.[5] .......... A61F 5/00

[52] U.S. Cl. .......... 606/241

[58] Field of Search .......... 128/71, 75; 272/134, 272/140, 144

[56] References Cited

U.S. PATENT DOCUMENTS

| | | | |
|---|---|---|---|
| 1,356,365 | 10/1920 | Hosmer | 128/75 |
| 2,984,238 | 5/1961 | Axtell et al. | 128/75 |
| 3,103,357 | 9/1963 | Berne | 272/134 |
| 3,167,068 | 1/1965 | Carr | 128/75 |
| 3,353,532 | 11/1967 | Ellis | 128/75 |
| 4,030,489 | 6/1977 | Buckner | 128/75 |
| 4,205,665 | 6/1980 | Burton | 128/68 |
| 4,269,279 | 5/1981 | Burton et al. | 128/75 |
| 4,396,012 | 9/1983 | Cobiski | 128/75 |
| 4,422,452 | 12/1983 | Burton | 128/75 |
| 4,569,340 | 2/1986 | Burton | 128/75 |
| 4,583,533 | 4/1986 | Goodley et al. | 128/75 |
| 4,603,689 | 8/1986 | Horner | 128/75 |
| 4,688,557 | 8/1987 | Bradstreet | 128/75 |
| 4,715,362 | 12/1987 | Scott | 128/75 |
| 4,746,116 | 5/1988 | Inada | 272/144 |
| 5,033,459 | 7/1991 | Burton | 128/71 |

FOREIGN PATENT DOCUMENTS

| | | | |
|---|---|---|---|
| 2363390 | 6/1975 | Fed. Rep. of Germany | 128/75 |
| 1371332 | 7/1964 | France | 128/75 |

*Primary Examiner*—Edgar S. Burr
*Assistant Examiner*—Moshe I. Cohen
*Attorney, Agent, or Firm*—Merchant, Gould, Smith, Edell, Welter & Schmidt

[57] ABSTRACT

A device (10) for transferring stress from the lumbar spine to a rib cage of a person is disclosed. The device (10) includes support members (60 and 61) for engaging and support the person below a rib cage. The supports bars (40 and 41) support the support members (60 and 61). The support bars are positioned substantially below the support members. A seat member (30) is positioned below the support members (60 and 61). The person assumes a seating position on the seat member (30) and is also supported thereby. A safety strap (120) is connected to the support members (60 and 61). The amount of support provided the person by the seat member and the support member may be varied. In addition, the invention includes a method of transferring stress utilizing the device (10). The device (10) may also provide the additional feature to gain physically beneficial exercise in conjunction with gravity traction.

19 Claims, 4 Drawing Sheets

FIG. 1
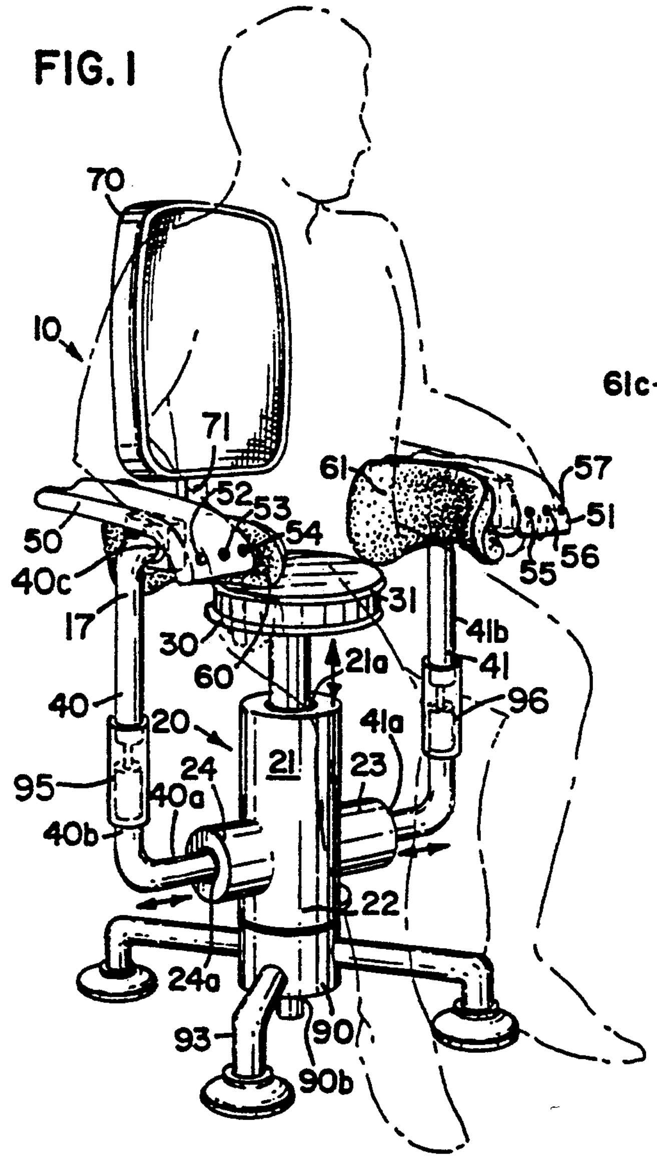
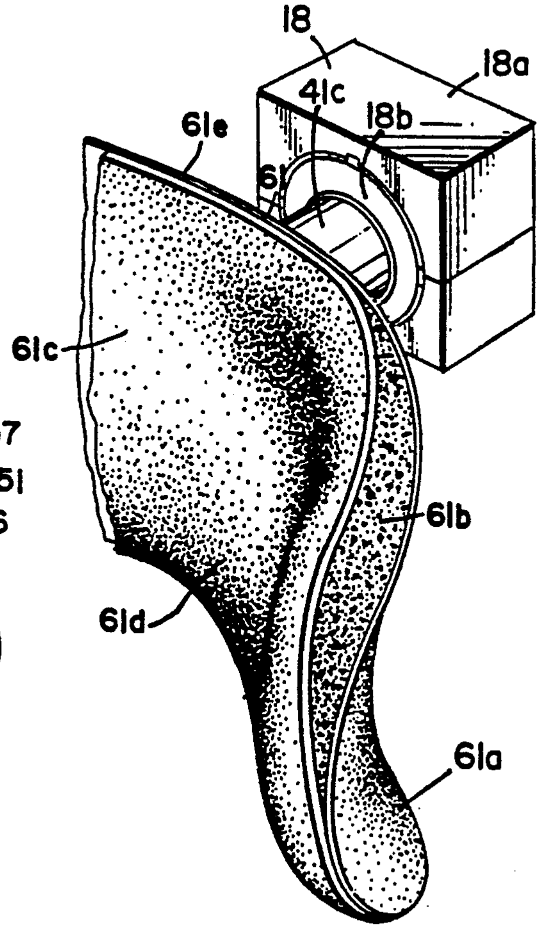
FIG. 3
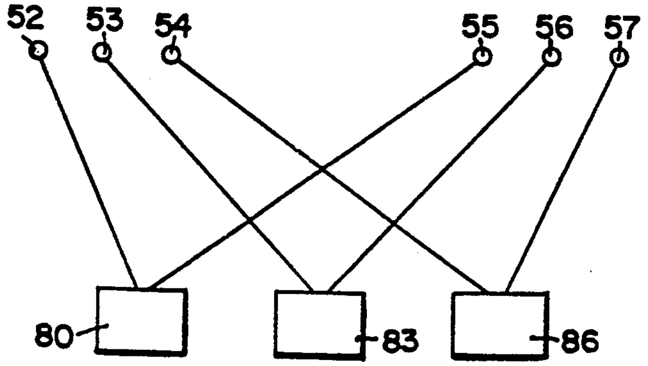
FIG. 5

FIG. 2
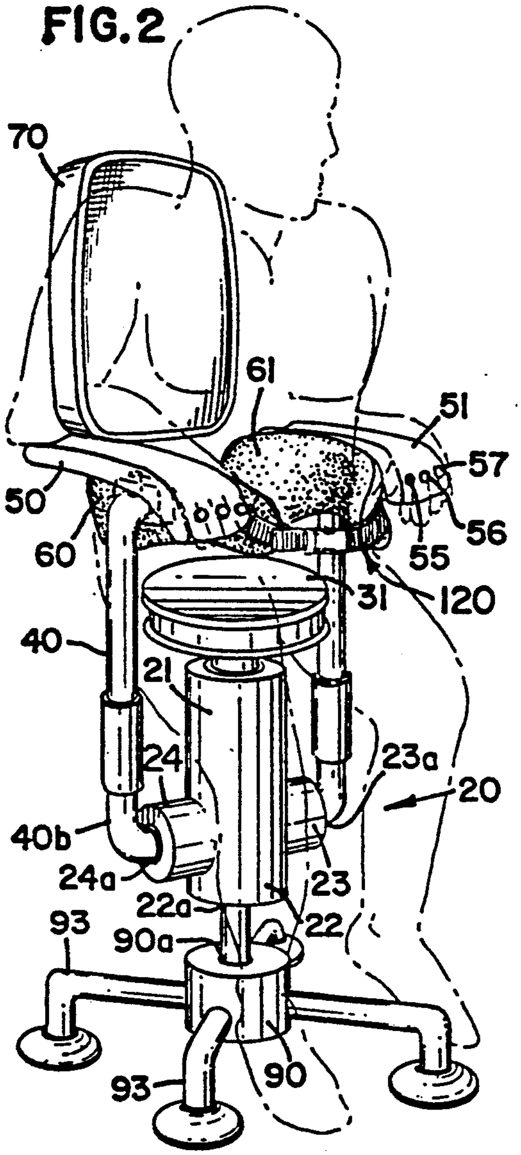
FIG. 7
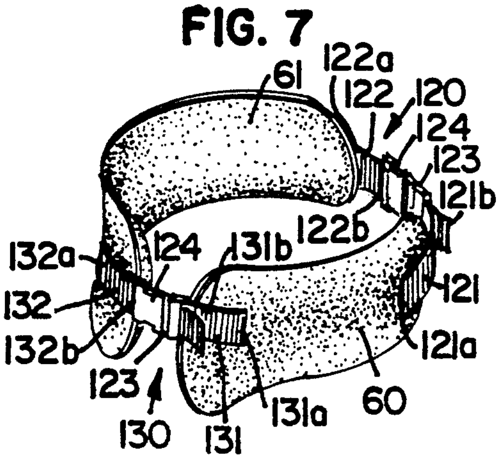
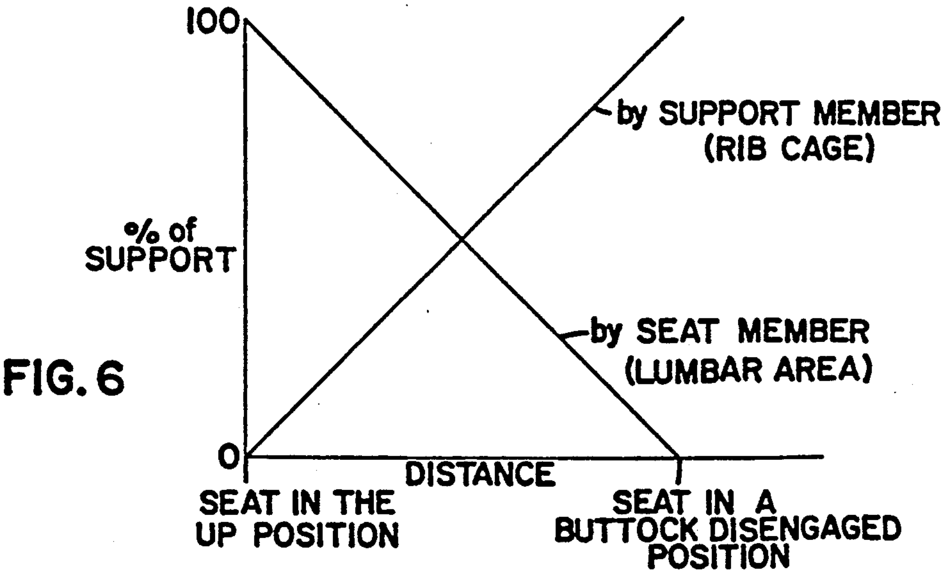
FIG. 6

FIG. 8
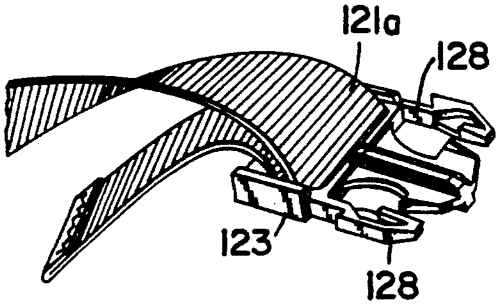
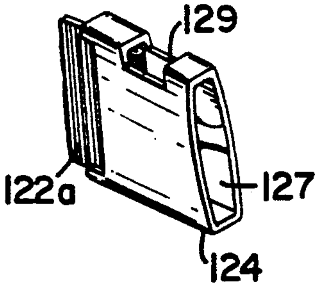
FIG. 9

GRAVITY TRACTION DEVICE WITH A SAFETY STRAP AND BASE SUPPORT AND METHOD

This application is a continuation-in-part of U.S. Ser. No. 07/609,065, filed Oct. 29, 1990 and issued July 23, 1991, as U.S. Pat. No. 5,033,459 pending, which is a continuation of Ser. No. 07/488,534, filed Feb. 28, 1990, now abandoned, which is a continuation of Ser. No. 07/301,172, filed Jan. 24, 1989, now abandoned.

FIELD OF THE INVENTION

This invention refers generally to a device for transferring weight stress from a lumbar spine to a rib cage of a person. More specifically, this invention relates to a gravity traction device having a means for supporting a support member, whereby the supporting means is positioned substantially below the support member and wherein the person begins using the device from the sitting position. The device also provides an apparatus for exercise relative to the disc tissue of the lumbar spine.

BACKGROUND OF THE INVENTION

Back pain is a common and significant malady afflicting large numbers of people and virtually every country of the world. The wide spread nature of the problem has been highlighted in numerous articles printed in both medical and news periodicals. Illustrative are articles entitled Bare-bones Facts About Your Aching Back from the December, 1980 issue of Readers Digest and the cover story from the July 14, 1980 issue of Time magazine.

Axial traction has been shown to be effective in treating certain types of low back ailments, in preventing back ailments and in producing low back health. Such traction has been found to be an effective means of realigning improperly aligned or displaced vertebral elements as well as their associated invertebral discs and soft tissues. Such traction has also been shown to reduce herniated contained intervertebral discs. Further, such traction has also been shown in muscle and ligament injury or insult to reduce spasm and inflammation, enhance blood flow and to promote optimal healing. Certain circumstances have, however, long presented obstacles to the effective application of controlled traction to the lumbar area. These circumstances include the significant amount of force which must be applied, the lack of a location at which the axially directed force can be applied, and the position of the person during which the axial force is being applied.

In 1971, the applicant provided for the construction of an apparatus to support a person, such person having one of a number of conditions such as a protruded lumbar disc, in a vertical position wherein the torso of the person was suspended by a chest harness encircling the rib cage. As a result of the research, the applicant has proven scientifically and conclusively demonstrated that the rib cage can serve as an optimum site of fixation and does serve well this purpose. He determined that, in order for the harness to function most effectively, it must, at its lower end, be tightened beneath the rib cage so that, as axial force is applied to the harness, the rib cage will not slide therethrough.

After continued research, the applicant invented an improved gravity traction vest. Prior to this time, the tightening of a lower most belt of the gravity vest was accomplished exclusively by providing a belt having a sufficient number of locking points whereby the belt could be tightened so that it was within the perimeter of the rib cage regardless of the size of the person being treated. Applicant invented the new improved gravity traction vest that provided means whereby axial fixation could be efficiently accomplished, yet wherein the treatment is not rendered uncomfortable. Applicant filed a patent application Ser. No. 299,679 on Sept. 8, 1981 for the improved gravity traction vest. This application was allowed on Aug. 17, 1983 and has been granted U.S. Pat. No. 4,422,452.

While the improved second generation gravity traction vest provided improvement over the original gravity traction vest, there remained a number of problems associated with its use. These problems included the need to tighten a number of cinctures to secure the vest to the person, the rough surfaces of the cinctures being felt through the vest by the person. While there was an improved locking of the vest to the person due to the cushion insert, it was desirable to provide for still more positive locking. The need to provide comfort to the person has always been a goal which each generation has tried to accomplish. The goal was to provide a vest which allowed the person to accept therapy and not cause discomfort. While there has been improvement in this area, there has been the need for still more improvement.

It is these problems in the prior art that a third generation gravity traction vest was developed. It provides for a torso surrounding member being constructed of the rigid material, a simple and effective means for securing the vest to the person and a flanged under portion that protrudes inwardly toward the person for engagement below both the lowest rib and the inverted U-shaped area of the rib cage. U.S. Pat. No. 4,569,340 was issued on Feb. 11, 1986 on such a vest.

While the inventor's vests have been utilized for many people and have proved quite successful, all of the vests to date have required overhead support of the vest. This is a drawback in that such devices are large and cumbersome and are best utilized in a hospital or clinic setting.

U.S. Pat. No. 3,353,532 issued to L. C. Ellis describes a traction apparatus wherein support is provided to a person by side members and does not utilize a vest which encircles the person's body. However, such a device has not proven to be practical in that there is no means for gradual force applied to the spine. Still further, the side members appear to work by a simple compression from just underneath the armpits of the person to just above the waist of the person.

The successful prior art devices have tended to be vests and have accordingly encircled the torso of the person using the device. Although the vests have been employed successfully, one of the inherent drawbacks of a vest is that a large portion of the torso is encircled and breathing can be somewhat restricted as the tightly cinched vest covers the rib cage. Further, because the torso is encircled, there is a greater heat build up for the person. Further, because of the total device design, the person is somewhat restricted from accomplishing movement of the body such that beneficial tissue exercise can not be accomplished.

The present invention addresses the problems associated with the prior art devices and provides for an effective means of transferring stress from a lumbar spine to a rib cage of a person starting in the seated position wherein no overhead support is necessary to support the device.

SUMMARY OF THE INVENTION

The present invention is a device for transferring stress from a lumbar spine to a rib cage of a person. The device includes a support member for engaging in supporting the person below the rib cage. Means for suspending the support member is also provided. The suspending means is positioned substantially below the person. A seat member is also provided and is positioned below the support member. The person assumes a sitting position on the seat member and the person is also supported thereby. Means for varying the amount of support provided the person by the seat member and the support member are cooperatively connected to the seat member and support member respectively, wherein a gradual transferring of stress from the lumbar spine to the rib cage may be effected. A safety strap is operatively connected to said support member.

In addition, the present invention is a method for transferring stress from a lumbar spine to a rib cage of a person including the person sitting on a seat member of the device described in the preceding paragraph. The support member is moved to an engaging position, whereby the support member is positioned below the rib cage and at a first distance from the seat member. Next, the distance between the seat member and the support member is increased, whereby support of the person is shifted, in a controlled manner, from the seat member to the support member. In a preferred embodiment, the distance is increased by lowering the seat member. Further, a flexible coupling member and spring-damper device are provided for rotational and vertical movement.

BRIEF DESCRIPTION OF THE DRAWINGS

FIG. 1 is a perspective view showing one embodiment of the present invention (shown without the safety strap).

FIG. 2 is a perspective view of the device shown in FIG. 1 with the seat in a lowered position and the housing in a raised position.

FIG. 3 is a perspective view of a portion of the support member and cradle of the device of FIG. 1 (shown without the safety strap).

FIG. 5 is a schematic view of the electrical controls of the present invention.

FIG. 6 is a graph showing the transfer of stress by a person using the device of FIG. 1.

FIG. 7 is a perspective view of the device shown in FIG. 1 showing only the support members and the safety straps.

FIG. 8 is a perspective view of the tongue member for the safety strap.

FIG. 9 is a perspective view of the buckle of the safety strap.

DETAILED DESCRIPTION OF THE PREFERRED EMBODIMENT

Figure 4:
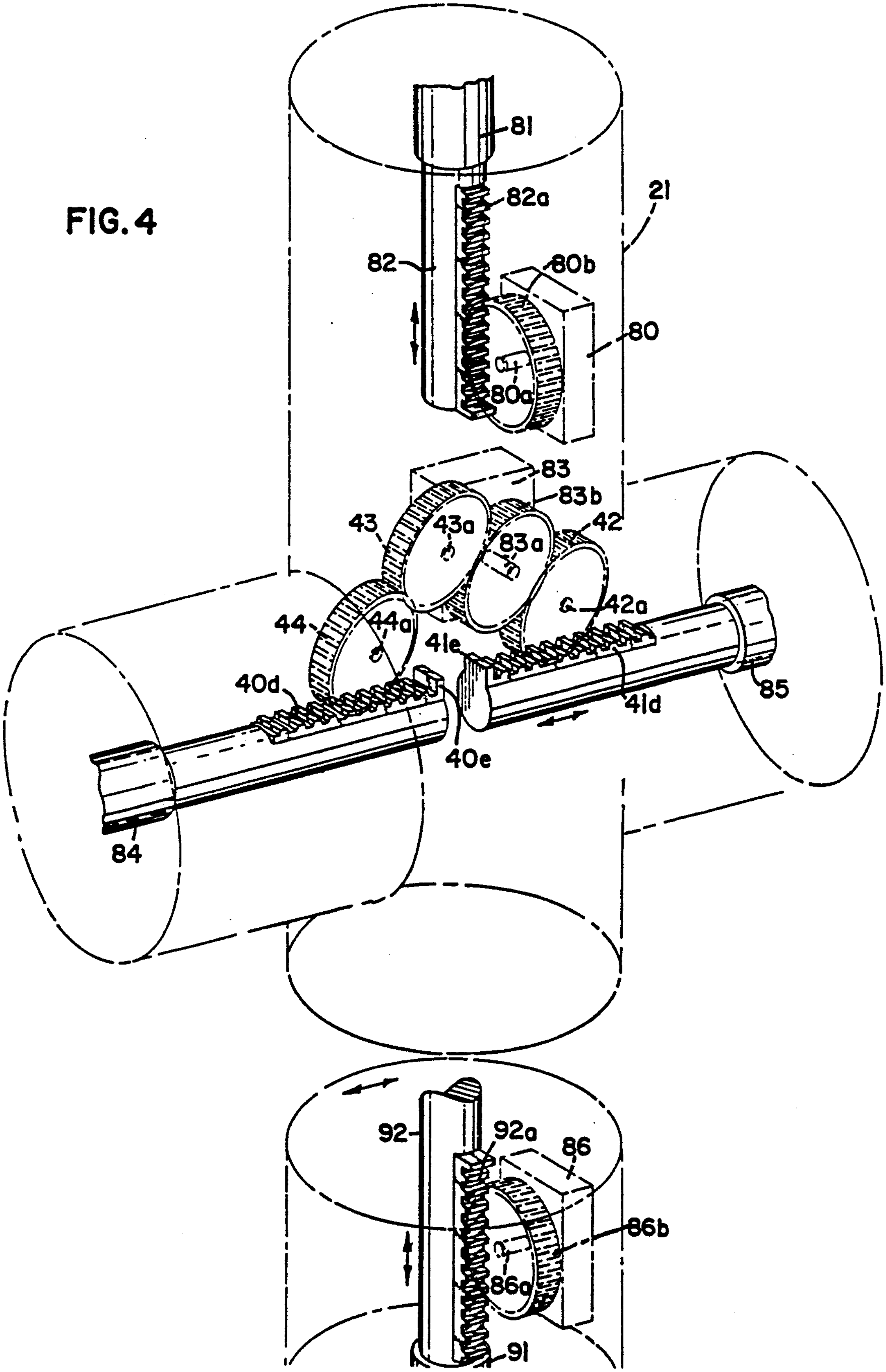
FIG. 4 is a perspective view of a portion of the device shown in FIG. 1 with the housing and base removed to show the working mechanisms.

Referring to the drawings, wherein like numbers represent like parts throughout the several views, there is generally disclosed at 10 a gravity traction device. The traction device 10 includes a housing 20. The housing 20 includes an upper cylindrical portion 21, lower cylindrical portion 22, a first side cylindrical portion 23 and second side cylindrical portion 24, all cooperatively connected to form the single housing 20. The housing 20 may be made of any suitable material which has sufficient structural support for a chair housing. The housing is hollow and has an inner cavity to house a variety of items to be discussed hereafter. Further, the upper cylindrical portion 21 has a circular opening 21*a*, lower cylindrical portion 22 has a cylindrical opening 22*a*, first side cylindrical portion 23 has a circular opening 23*a* and the second side cylindrical portion 24 has a circular opening 24*a*. An electrical drive motor 80 is cooperatively connected, by well known means, such as brackets and screws, to the inside of the upper cylindrical portion 21. The motor 80 has a shaft 80*a* which, when it rotates, causes the gear 80*b* to rotate. A sleeve 81 is mounted in the circular opening 21*a* and a cylindrical shaft 82 is positioned in the sleeve 81 for longitudinal movement. The cylindrical shaft 82 has a rack gear 82*a* which engages the gear 80*b*. A seat member 30 is cooperatively connected to a top end of the cylindrical shaft 82. This may be accomplished by any means well known in the chair industry, such as having the top of cylindrical shaft 82 threaded and have a mating thread in the bottom of the seat member 30, wherein the seat member 30 is simply screwed on to the top of the cylindrical shaft 82. The seat member 30 is shown in the figures as being a circular disk, but it is understood that any suitable shape may be utilized. Still further, the seat member 30 may have a cushioned top 31 cooperatively attached thereto.

A first support bar 40 has a first generally horizontal leg 40*a* cooperatively connected to a generally upright member 40*b*, which is in turn cooperatively connected to a top generally horizontal leg 40*c*. The generally upright member 40*b* may optionally be split into two components and a spring-damper device 95 inserted between the two components. The device 95 is a shock absorber which will allow vertical movement by allowing the two components of 40*b* to be moved toward and away from each other. The spring damper portion of the device 95 has a first end connected to the top portion of 40*b* and its bottom portion connected to the bottom portion of 40*b*, thereby being inserted into the length of the member 40*b*. An outer sleeve is placed over the spring damper mechanism to provide stability and not allow for rotational movement. A second support bar 41 has a first generally horizontal leg 41*a* cooperatively connected to a generally upright member 41*b*, which is in turn cooperatively connected to a top generally horizontal leg 41*c*. A spring damper device 96 may similarly be connected to the upright member 41*b*. An electric drive motor 83 is cooperatively connected to the inner cavity of the housing 20 by any appropriate configuration of brackets and hardware, such as screws. A bearing 84 is cooperatively connected into the circular opening 24*a* and a bearing 85 is cooperatively connected into the circular opening 23*a*. The electric drive motor 83 has a shaft 80*a* to which is cooperatively connected a drive gear 80*b*. Horizontal leg 40*a* has a rack gear 40*d* cooperatively connected to it. The rack gear 40*d* has a stop 40*e* at one end. Similarly, a rack gear 41*d* is cooperatively connected to the horizontal leg 41*a*. The rack gear 41*d* also has a stop 41*e* at one end. A gear 42 is positioned between the gear 80*b* and the rack gear 41*d* and is mounted, by means well known but not shown, on a shaft 42*a*. Similarly, gears 43 and 44 are mounted between the drive gear 80*b* and the rack gear 40*d*. Gears 43 and 44 are mounted on their respective shafts 43*a* and 44*a*, by means well known in the art, but not shown.

Arm rest 50 and 51 are respectively connected to a top surface of cradles 17 and 18. Any suitable means may be utilized to cooperatively connect the arm rests to the cradles 17 and 18, such as a spot weld. The arm rests may be of any suitable configuration to comfortably support the person's lower arm. The cradles 17 and 18 are similar, and therefore only cradle 18 will be discussed in further detail. The cradle 18 has an outer housing assembly 18*a* which surrounds and is cooperatively connected to a TORSILASTIC spring 18*b*. The TORSILASTIC spring 18*b* may be of a suitable type such as that supplied by the BF Goodrich Company of Akron, Ohio. The TORSILASTIC spring will allow for rotational movement and provides for a flexible rotatable coupling. The TORSILASTIC spring 18*b* has an inner opening sized and configured to match the size and configuration of the horizontal leg 41*c*. While not shown in FIG. 7, the horizontal leg 41*c* extends out the back of the cradle 18 and is cooperatively connected to the generally upright member 41*b*. The TORSILASTIC spring 18*b* has an inner opening sized and configured to match the size and configuration of the horizontal leg 41*c*. The support bar is placed inside of the TORSILASTIC spring 18*b* when in use, as shown in FIG. 3. The TORSILASTIC spring is an integral unit consisting of an inner metal shaft surrounded by a molded rubber cylinder with an outer shell of high strength metal alloy. The cylinder is strongly bonded to both the inner shaft and the outer shells forming a compact, lightweight unit. When the support bar 41*c* is inserted into the opening, spring action occurs when one of the middle components is rotated (caused by the rotation of the support bar 41*c*) in relationship to the other. The rubber resists this deformation and returns to the original position when the force is released. Thereby, a rocking or rotation motion may be imparted by the wearer. Similarly, the support bar 41*a* is configured and attached to the cradle 17. As will be more fully discussed hereafter, control buttons 52, 53 and 54 are placed on the arm rest 50 and control buttons 55, 56 and 57 are placed on the arm rest 51.

A support member 60 is cooperatively connected to the end of the horizontal leg 40*c* and a support member 61 is cooperatively connected to the end of the horizontal leg 41*c*. The support members 60 and 61 are mirror images of one another. Therefore, the description of the support member 61 is equally applicable to the support member 60. As shown in FIG. 3, the horizontal leg 41*c* is cooperatively connected to the outside surface 61*a* of the support member 61. The outside surface 61*a* may be of any suitable material such as a polymeric material such as a rigid moldable plastic of a suitable thickness to support the person, i.e., ¼" A.B.S. plastic. A pad 61*b*, preferably of a semirigid polymeric material, such as a high density closed cell foam rubber, is placed between the outer surface 61*a* and the inner surface 61*c*. It is understood any cushioning material, such as an air bladder, may also be utilized. The inner surface 61*c* is typically constructed of semirigid polymeric material, somewhat harder than the foam 61*b*, but still exhibiting an ability to conform to the person's profile. An optional removable cover may enclose the support member 61. The cover would be soil resistant, such as a nylon cloth. While a three core structure is shown, other suitable configurations may be utilized. The three core structure may be suitably bonded together by an appropriate adhesive. The semi-rigid polymer such as foam 61*b* is inserted in the appropriate places, as shown in FIG. 3, to form a support which comfortably fits under the rib cage of the wearer. The portion of the support 61 which would fit immediately under the rib cage is the protrusion 61*d* and this protrusion 61*d* would ultimately provide the support under the rib cage of the person, as will be more fully described hereafter. While the above-noted construction is preferred, it is understood that other suitable shapes may be utilized. This may include shape where there is no protrusion 61*d* and that the person is supported by the top edge 61*e* underneath the person's rib cage. Applicant has found that a protruding foam pad in the middle of the support member 61 provides for more comfortable support. The teachings of Applicant's prior patent with respect to support may be utilized in developing alternate embodiments of a suitable support.

The support bars 40 and 41 are positioned substantially below the support members 60 and 61 respectively. By providing support from below the support members 60 and 61, a gravity traction device is possible without the overhead support mechanism of the prior art. This enables for a gravity traction device in the general configuration of a chair and therefore leads to the application of the device in many settings including but not limited to the home, office and/or workplace.

The gravity traction device 10 also includes a back support 70 which is cooperatively connected to either the seat member 30 or the housing 20. It is not critical that there be a back member 70, but Applicant has found that it does provide for a more comfortable position for the person. As shown in FIG. 1, the back member 70 is cooperatively connected to a downwardly depending arm 71 which is in turn cooperatively connected to the seat member 30.

The gravity traction device 10 also includes a lower housing 90. The lower housing 90 has a top circular opening 90*a* and a bottom circular opening 90*b*. A bearing 91 is cooperatively positioned in the bottom circular opening 90*b* and a shaft 92 moves vertically through the bearing 91. The top of the shaft 92 is cooperatively connected in the circular opening 24*a* so that vertical movement of the shaft 92 causes a corresponding vertical movement of the housing 20. Four support feet 93 are cooperatively connected to the lower housing 90 and provide stabilization support for the gravity traction device 10. An electrical drive motor 86 is cooperatively connected to the inside of the lower housing 90 by a suitable arrangement of bracket and mounting hardware, not shown. The electric drive motor 86 has a shaft 86*a* on which a gear 86*b* is mounted. The gear 86*b* engages a rack gear 92*a*. The rack gear 92*a* is cooperatively connected to the shaft 92 by any suitable mounting means.

A schematic of the electrical controls is shown in FIG. 5. Control buttons 52 and 55 are electrically connected to the drive motor 80, control buttons 53 and 56 are electrically connected to the drive motor 83 and control buttons 54 and 57 are electrically connected to the drive motor 86. Depression of the control button 52 will cause the drive motor 80 to operate in a clockwise direction as shown in FIG. 4. When the shaft 80 rotates in a clockwise direction, the gear 80*b* causes a corresponding movement of the rack gear 82*a* and causes the shaft 82 to go in an upward direction. Release of the control button 52 will cause the motor 80 to stop. Depression of the control button 55 causes the motor 80 to rotate in a counterclockwise direction and thereby causes the shaft 82, and therefore the seat 30, to go downward. Release of the button 55 will cause the motor 80 to stop.

Depression of button 53 causes motor 83 to turn in a clockwise direction and depression of button 56 causes motor 83 to turn in a counter clockwise direction. Clockwise rotation of the gear **80*b* will cause gear 42 to rotate counterclockwise and thereby push the support bar 41 in an outward direction. The same clockwise rotation of 80*b* will cause gear 43 to rotate in a counterclockwise direction and gear 44 to rotate in a clockwise direction. This in turn will cause the support bar 40** to also go in an outward direction.

Depression of button 56, which causes motor 83 and therefore the gear **80*b* to rotate in a counterclockwise direction and will cause gear 42 to operate in a clockwise direction thereby bringing the support bar 41 inward. The same counterclockwise rotation of 80*b* causes gear 43 to rotate clockwise and 44 counterclockwise, thereby bringing support bar 40 also inward. The support members 60 and 61 will, of course, move in the same direction as the support bars 40 and 41. Release of buttons 53 and 56 will cause the motor 83** to stop.

Depression of control button 54 causes motor 86 to rotate clockwise and also clockwise rotation of gear **86*b*, thereby moving the shaft 92 upwards. Depression of button 57 causes counterclockwise rotation of motor 86 and gear 86*b* and thereby a downward movement of shaft 92. Release of buttons 54 and 57** will cause the motor to stop.

The use of a safety strap may be desirable for certain persons, such as those with serious physical disabilities, mental incapacity or the infirmed for an extra measure of restraint. Referring to FIG. 7, it can be seen that a first safety strap 120 is operatively connected to the fronts of the support members 60 and 61 and a second support strap 130 is operatively connected to the backs of the support members 60 and 61. It is of course understood that two safety straps may be utilized as shown, or alternately, only a front safety strap or only a rear safety strap may be used. Further, while a specific embodiment of safety straps 120 and 130 is shown, it is understood that other suitable safety straps may also be utilized. For example, instead of the safety strap shown, the strap could simply be fastened to one of the support members and a loop fastened to the other support member. The strap could be slid through the loop, pulled tight and fastened back on itself. Any other suitable strap could of course be utilized.

The specific embodiment in FIG. 7 shows the safety strap 120 having a first strap 121 having a first end **121*a* operatively connected to the first support member 60 by means well known in the art. This may be done by means of either a fastener, stitching the strap to the support member, or other well known means. The second strap 122 has a first end 122*a* operatively connected to the second support member 61 by means well known in the art. A fastener is utilized to operatively connect the second end 121*b* of the first strap 121 to the second end 122*b* of the second strap 122. A fastener includes a suitable tongue member 123 operatively connected to the second end 121*a* and a buckle 124 operatively connected to the second end 122*b*. While any suitable fastener may be utilized, the fastener shown is preferred in that it provides for a quick release. The tongue member 123 has deformable fingers 128 which are compressed and slid into the receiving hole 127 of the buckle 124. Once inserted, the fingers spring back and extend through locking holes 129 in the buckle 124. The length of the strap 121 is easily adjusted (as shown in FIG. 8**) dependent upon the size of the wearer.

A similar strap 130 is operatively connected between the backs of the support members 60 and 61. Like strap 120, the strap 130 has a first strap 131 and a second strap 132. The first end **131*a* is operatively connected to the first support member 60 and the first end 132*a* of the second strap is operatively connected to the second support member 61. A fastener comprising a tongue 123 operatively connected to the second end 131*b* and a buckle 124 operatively connected to the second end 132*b*** is provided. As previously stated, other embodiments of a safety strap may be utilized, particularly in the back where a strap that is more easily adjustable may be helpful for some person as they may not be able to easily reach behind themselves and buckle the back fastener.

While the foregoing describes a device having electrical motors and gears for effecting the movement of the support member and seat member, it is understood that this is just one example of many configurations that the present invention may take. For instance, the mechanisms could also be operated pneumatically, electro magnetically or manually.

In operation, the person sits on the seat member 30 in a normal fashion and is supported in a seated position. The initial height of the seat member 30 is adjusted such that when the support members 60 and 61 are brought inward, the person is supported by the support members just under the rib cage at the rib cage's lower rim. Initially, the shaft 92 and the lower housing 90 is positioned such that the person's feet are able to touch the ground. Once the person is seated on the seat member 30, control button 56 is activated, thereby moving the support members 60 and 61 inward, from a disengaged position, toward opposite sides of the person's rib cage. The person continues pressing control button 56 down until the desired level of force is applied by the support members underneath the person's rib cage to reach the engaged position. At this point, there is a first distance between the seat member and support member and the person is fully supported by the seat member. Control button 55 is then depressed, lowering the seat member 30. This increases the vertical distance between the seat member and support member to a second distance, which is greater than the first distance. The person is able to thereby selectively transfer a portion of the weight from the seat means to the support means, thereby allowing the weight of the person below the rib cage to provide traction to the person's spine. By lowering the seat member 30, the amount of support given to the person by the seat member 30 is reduced and support is correspondingly increased by the support members 60 and 61. The seat member 30 may be progressively lowered and even lowered sufficiently enough to disengage from the buttock of the person. When the seat member is disengaged, the amount of traction is determined by the weight of the lower extremities of the person as well as any weights which may be added to the person. Applicant has found that it is typically best to add the weights around the waist of the user.

FIG. 6 shows a graph which clearly indicates the transfer of stress as the seat member 30 is lowered. When the seat member 30 is in its up position, all of the person's weight using the device is being supported by the seat. Accordingly, the stress in the lumbar area is 100%. As the seat is lowered, the stress is transferred from the seat member 30 to the support members 60 and 61. For each percentage decrease by the seat member, there is a corresponding increase by the support members 60 and 61. As can be seen at the end of the graph, where the seat member 30 is in a disengaged position from the buttocks, the support is 100% from the support members 60 and 61 and no support from the seat member 30. When there is no support by the seat member 30, the lumbar area is in an unloaded condition, thereby allowing for effective treatment.

Typically, when a person first begins using the gravity traction device, the person is not able to tolerate a complete disengagement of the seat member 30. Therefore, the person only lowers the seat member 30 a small amount, thereby transferring only a small amount of force to the support members 60 and 61. In such a situation, only a small amount of stress from the lumbar spine is transferred to the rib cage. As the person progresses, the person is able to lower the seat further until the seat is able to finally disengage from the buttock of the person. At that time, weight may be added to the person to further increase the amount of traction to the lumbar spine.

As the seat member 30 is gradually lowered, the person may find himself being supported by the person's feet on the floor. At such time, the person has the option of depressing control button 54 to raise the housing 20, and thereby both the seat member 30 and supports 60 and 61 to a higher position to raise the person's feet off of the floor and thereby provide for no support from the person's feet. The person's arms are generally supported in an L-shaped position by the supports 50 and 51.

With the present invention, normal productive activities may be maintained in the seated position which can now actually become a position of suspension utilizing the rib cage of the chest as the point of fixation. The invention represents a unique means by which the normal stress and loading of the sitting position can be moderated, eliminated, or converted into a healthy zero weight stress influence on the lumbar spine. While the invention has been shown as a free standing chair, it may also be utilized in many other areas such as in motor vehicles, airplanes, or other seating configurations to allow the person to perform productive tasks while receiving treatment. Still further, the invention has been shown wherein the transfer of support is accomplished by the lowering of the seat member 30. It is also understood that the same transfer may be accomplished by the raising of the support members 60 and 61 and keeping the seat stationary, or a combination of both. By utilizing different methods to transfer support, the present invention may more easily be adapted to existing chairs, seats or benches.

A combination of the spring dampening devices 95 and 96 and the TORSILASTIC springs in the cradles 17 and 18 allow for the wearer to obtain beneficial exercise while at the same time transferring stress and loading from the lower spine to the rib cage. The wearer can shift his weight up and down in a jumping motion to provide for vertical motion. The spring dampening devices 95 and 96 dampen any such movement and return the apparatus back to its original position. This up and down motion provides exercise relative to the disc tissue of the lumbar spine. Still further, the wearer may rock forward and backward. The TORSILASTIC springs in the cradles 17 and 18 will ultimately restrict the forward motion and then cause the wearer to go back to an original upright position. This also promotes exercise of the disc tissue of the lumbar spine and reduces spasm and inflammation, enhance blood flow to provide optimal healing for muscle and ligament injury or insult.

It is also appreciated that the apparatus may include only one of these exercise features as opposed to both. Still further, it is understood that other ways of providing exercise may be utilized. One such method would be to not use a shock absorber device, but instead to have the bars 40*c* and 41*c* be slightly flexible which would allow for up and down motion and thereby exercise of the disc tissue.

Still further, it is appreciated that the exercise component could be supplied by many other suitable devices, such as a motor driven apparatus.

Still further, it has been found that this device stabilizes the thoracal lumbar junction.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as present herein All alternative modifications and variations of the present invention which follow in the spirit and broad scope of the appended claims are included.

I claim:

1. A device for transferring stress, starting from a seated position, from a lumbar spine to a rib cage of a person, the device comprising:

(a) a support member for engaging and supporting the person below the rib cage;

(b) means for supporting the support member, said support means including means for progressively moving the support member inward toward the person from a disengaged position to an engaged position, said supporting means being capable of maintaining the support member in the engaged position without use of a person encircling cinch strap connected to the support member;

(c) a seat member positioned below the support member, on which the person assumes a sitting position with the person being temporarily supported thereby;

(d) means for varying the amount of support provided to the person by the seat member and the amount of support provided by the person by the support member, said varying means including means to vary a distance between the seat member and the support member; and (e) a safety strap operatively connected to said support member.

2. The device of claim 1, wherein the support member comprises first and second support members for engaging the person on opposite sides.

3. The device of claim 2, wherein said support members have a rotation for being positioned under the rib cage.

4. The device of claim 2, wherein the supporting means comprises a first support bar cooperatively connected to the first support member and a second support bar cooperatively connected to the second support member.

5. The device of claim 1, further comprising means for moving the support member between disengaged and engaged positions.

6. The device of claim 1, wherein said supporting means being positioned substantially below the support member.

7. The device of claim 4, further comprising means for permitting controlled rotational movement of said support bars, wherein the person may exercise while also transferring stress.

8. The device of claim 1, further comprising means for allowing controlled vertical movement of the person while being supported, wherein the person may exercise while also transferring stress.

9. A support member for engaging and supporting the patient below the rib cage comprising:

(a) first and second support members for engaging and supporting the person on opposite sides, below the rib cage, the support members having a protrusion being positioned under the rib cage;

(b) a first support bar cooperatively connected to the first support member and a second support bar cooperatively connected to the second support members, said bars for supporting the support member, said support bars being positioned substantially below the support members;

(c) means for moving the support member, said support means including means for progressively moving the support member inward toward the person from a disengaged positioned to an engaged position, said support means being capable of maintaining the support member in the engaged position without use of a person encircling cinch strap connected to the support member;

(d) a seat member positioned below the support members, on which the patient assumes a sitting position with the patient being temporarily supported thereby;

(e) means for varying the amount of support provided to the patient by the seat member and the amount of support provided to the person by the support members said means for varying operatively connected to the seat member, wherein the seat members is gradually lowered, by the means for varying, to transfer the stress from the lumbar area to the support members; and (f) a safety strap having a first end operatively connected to said first support member and a second end operatively connected to said second support member.

10. The device of claim 9, wherein said strap comprises a first and second strap having first and second ends, said first end of said first strap operatively connected to said first support member and said first end of said second strap operatively connected to said second support member and further comprising means for operatively connecting said second end of said first strap to said second end of said second strap.

11. The device of claim 9, wherein said first and second support members each have a front and a back and said safety strap comprises a first strap operatively connected between said fronts of said first and second support members and a second strap operatively connected between said backs of said support members.

12. A device for transferring stress from a lumbar spine to a rib cage of a person, and also allowing exercising, the device comprising:

(a) a support means for engaging and supporting the person below the lower rim of the person's rib cage, the support means including generally upright members operatively connected to a support member;

(b) means for progressively moving the support member inward toward the person to an engaged positioned and maintaining the support member in the engaged position without use of a person encircling means connected to the support member, wherein there is a transfer of stress from the person's lumbar spine to the support member;

(c) means for allowing movement of the device, and thereby the person also, wherein the person may exercise the lumbar spine as well as transfer stress simultaneously said movement means permits generally vertical movement by cyclically shortening said upright members; and (d) a safety strap operatively connected to said support means.

13. The device of claim 12, wherein the movement means permits rotational movement of the person.

14. The device of claim 12, wherein the movement means permits generally vertical movement of the person.

15. The device of claim 12, wherein the movement means permits both rotational and vertical movement of the person.

16. A method of transferring stress, starting from a seated position, from a lumbar spine to a rib cage of a patient comprising:

(a) providing a device for seating a person on a seat member of said device comprising:

(i) a support member;

(ii) means for suspending the support member, the suspending means being positioned substantially below the person, said suspending means including means for progressively moving the support member inward toward the person from a disengaged position to an engaged position, said support means being capable of maintaining the support member in the engaged position without use of a person encircling cinch strap connected to the support member;

(iii) the seat member positioned below the support member;

(iv) means for varying the amount of support provided to the person by the seat member and the support member, said varying means including means to vary a distance between the seat member and the support member; and (v) a safety strap operatively connected to said support member;

(b) moving progressively the support member to an engaging position, whereby the support member is positioned below the rib cage and at a first distance from the seat member said supporting member maintained in an engaged position without the use of a person encircling cinch connected to the support member; and (c) increasing to a second distance the seat member from the support member, whereby support of the person is shifted, in a controlled manner, from the seat member to the support member.

17. The method of claim 16, wherein the seat is lowered to shift support from the seat member to the support member.

18. The method of claim 16, further comprising moving the person in a generally vertical plane by cylindrically shortening upright members which are a portion of the suspending means.

19. The method of claim 16, further comprising moving the person rotationally.

* * * * *